US00PP35783P3

(12) United States Plant Patent
Sanabria Aguilar et al.

(10) Patent No.: US PP35,783 P3
(45) Date of Patent: Apr. 30, 2024

(54) BLUEBERRY PLANT VARIETY NAMED 'BLUECSOL12'

(50) Latin Name: ***Vaccinium corymbosum* L.**
Varietal Denomination: BLUECSOL12

(71) Applicant: CAMPOSOL S.A., Lima (PE)

(72) Inventors: Kimberlayn Maria Apsara Sanabria Aguilar, Lima (PE); Milagros Janet Granda Mogollon De Montoya, Lima (PE); Luis Jose Montgomery Taboada, Lima (PE); Jorge David Romero Pajares, Lima (PE)

(73) Assignee: CAMPOSOL S.A., Lima (PE)

( * ) Notice: Subject to any disclaimer, the term of this patent is extended or adjusted under 35 U.S.C. 154(b) by 0 days.

(21) Appl. No.: 17/803,911

(22) Filed: Jan. 17, 2023

(65) Prior Publication Data

US 2023/0270030 P1 Aug. 24, 2023

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ... A01H 5/08; A01H 5/00; A01H 6/36; A01H 6/368
See application file for complete search history.

*Primary Examiner* — June Hwu
(74) *Attorney, Agent, or Firm* — LADAS & PARRY LLP

(57) ABSTRACT

A new and distinct evergreen blueberry variety with zero chill requirement named 'BLUECSOL12', characterized by the following combination of traits: medium to strong plant vigor, upright growth habit, ovate leaf shape, campanulate corolla shape and moderate conspicuousness of ridges on corolla tube, oblate fruit shaped, extra-large fruit-size, moderate bloom intensity, high sweetness and acidity, and firm fruit. Latin name of the genus and species: *Vaccinium corymbosum* L.

6 Drawing Sheets

Latin name: *Vaccinium corymbosum* L.
Variety denomination: Blueberry plant named 'BLUECSOL12'.

CROSS REFERENCE TO RELATED APPLICATIONS

This application claims priority to a Peruvian Breeder's Rights Application No. 94-2022 filed on Jan. 19, 2022, the entire contents of which is incorporated by reference herein.

BACKGROUND OF THE INVENTION

The present invention relates to a new *Vaccinium corymbosum* L. plant, which was selected from open pollination between 'Biloxi' (*Vaccinium corymbosum* L., public plant) as the female (seed) parent and pollen from an unidentified variety (*Vaccinium corymbosum* L.). Berry seeds of plants of the 'Biloxi' variety were collected from different fields , located in Viru, La Libertad, Peru at the beginnings of 2016. 11805 seedlings at high density were planted under field conditions in December of the same year.

The seedlings were evaluated during 3 growing season (2017, 2018 and 2019) and the breeding method used was phenotypic recurrent selection. In December 2019 one of the seedlings, 'BLUECSOL12', was isolated due to its excellent quality fruit, long postharvest life, and high yield potential. 'BLUECSOL12' was asexually propagated by softwood cuttings to confirm the distinctness, and stability of the characteristics observed in another growing season. 5 rooted cuttings were planted in an experimental test plot, located in Viru, La Libertad, Peru. From December 2020 until the present, said test plot has shown that the unique features of this new *Vaccinium* variety are stable and reproduce true to type in successive generations of asexual propagation. In addition, 'BLUECSOL12' was subsequently propagated by softwood cutting and tissue culture, and an additional plot with 430 plants was planted in December 2021 at the same location. This new plot has maintained up to the present the distinctness and stability characteristics of the new variety of *Vaccinium corymbosum* L.

SUMMARY OF THE VARIETY

The following is the summary of the description of the new and distinct variety of blueberry 'BLUECSOL12', which was selected in, Viru, La Libertad, Peru in December 2019. 'BLUECSOL12' has not been observed under all environmental conditions. The phenotype may vary somewhat with variations in the environmental conditions such as temperature and light intensity, without, however, any variance in genotype. 'BLUECSOL12' is an evergreen blueberry variety with zero chill requirement. The following are the most distinguishing traits of this new variety: medium plant vigor, upright growth habit, ovate leaf shape, campanulate corolla shape and moderate conspicuousness of ridges on corolla tube, oblate fruit shaped, extra-large fruit-size, moderate bloom intensity, high sweetness and acidity, and firm fruit.

'BLUECSOL12' was selected as a mid-late variety, with solid yield potential, excellent fruit quality, flavor, and post-harvest life.

BRIEF DESCRIPTION OF THE DRAWINGS

The accompanying color photographs show typical bush, leaves, flower, and fruit characteristics of the new *Vaccinium*

*corymbosum* L. 'BLUECSOL12'. Colors shown are as accurate as can be reasonably reproduced by the photographic means. Photographs were taken of 2 and 5-year-old plants grown in fields of the test plot located in Viru, La Libertad, Peru.

DETAILED BOTANICAL DESCRIPTION

Figure 1:
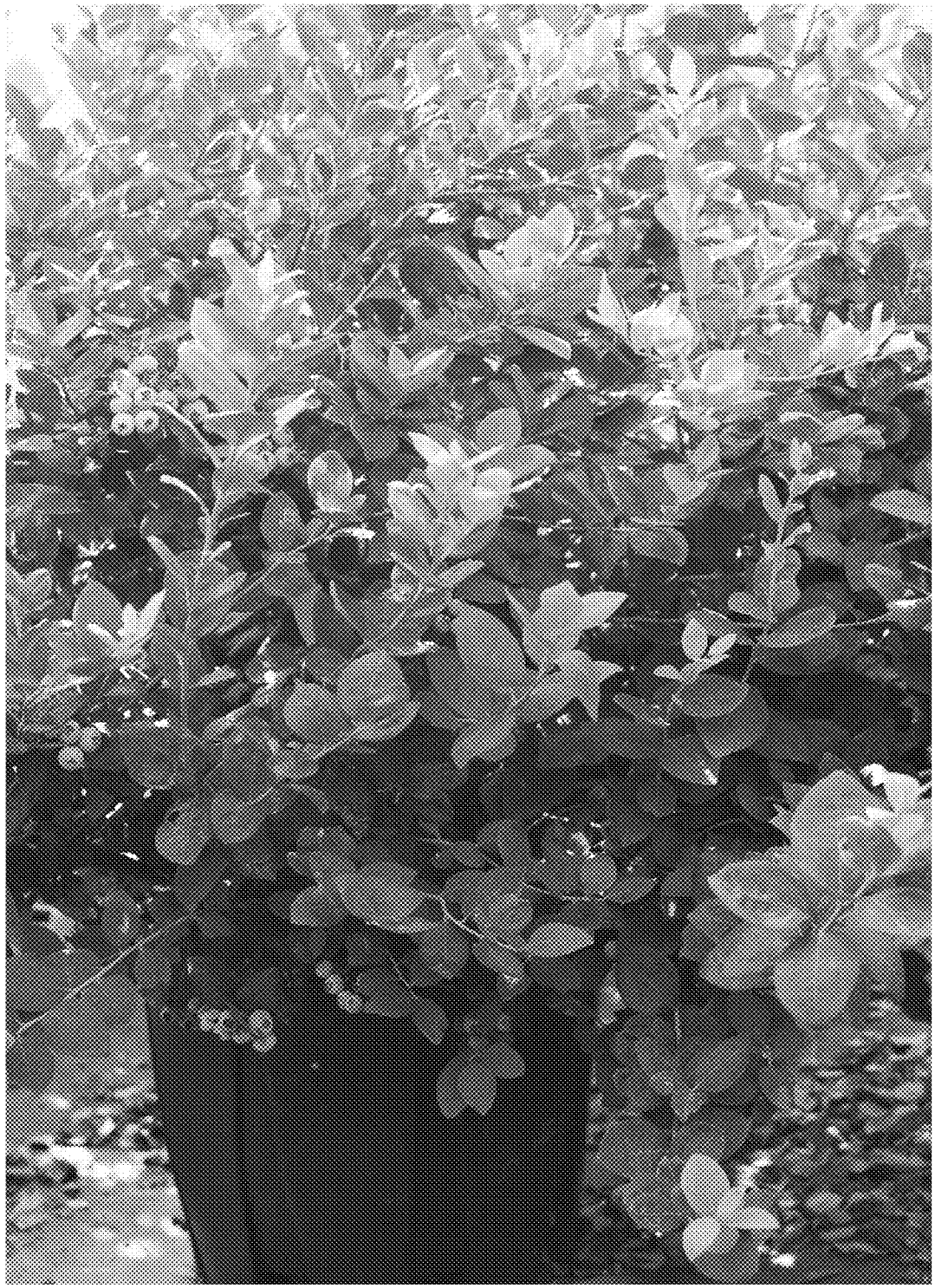
FIG. 1.—Shows typical bush with upright growth habit on 5-year-old plant of the new variety 'BLUECSOL12'.
Figure 2:
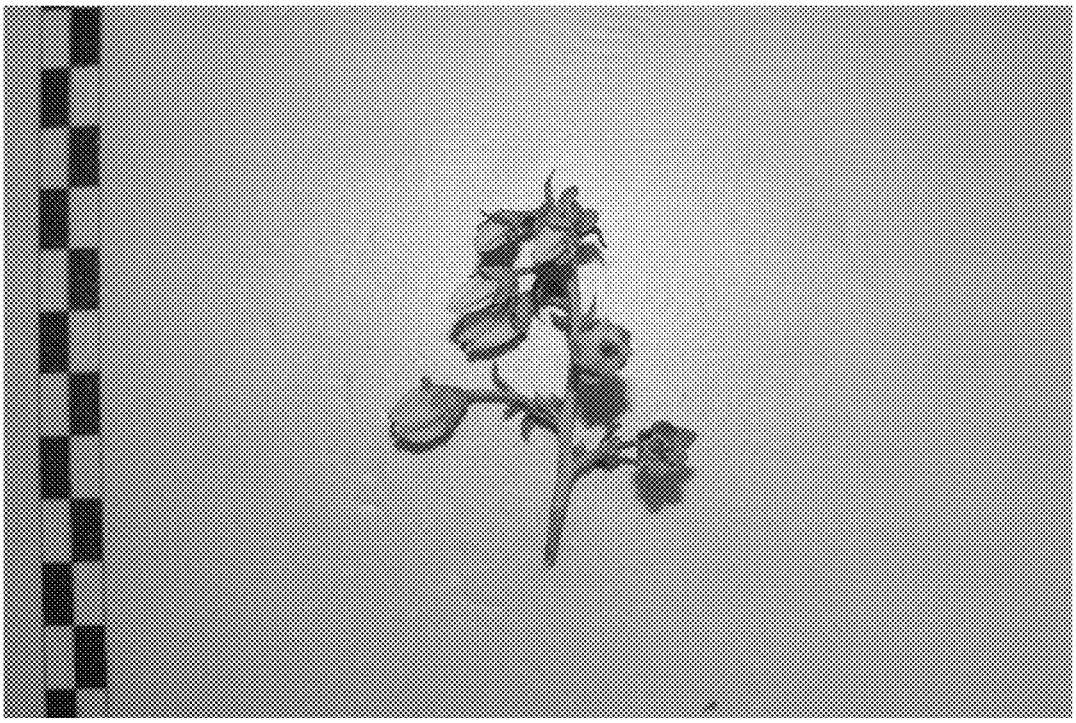
FIG. 2.—Shows the inflorescence length on 2-year-old plant of the new variety 'BLUECSOL12'.
Figure 3:
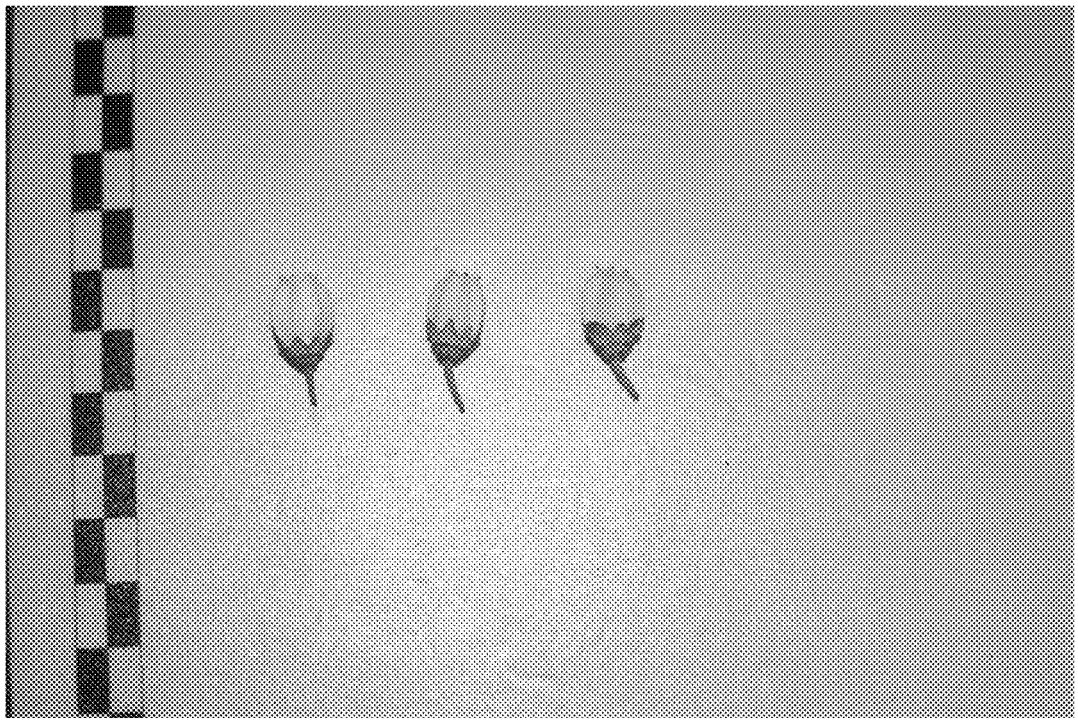
FIG. 3.—Shows the size and shape of the flower corolla on 2-year-old plant of the new variety 'BLUECSOL12'.
Figure 4:
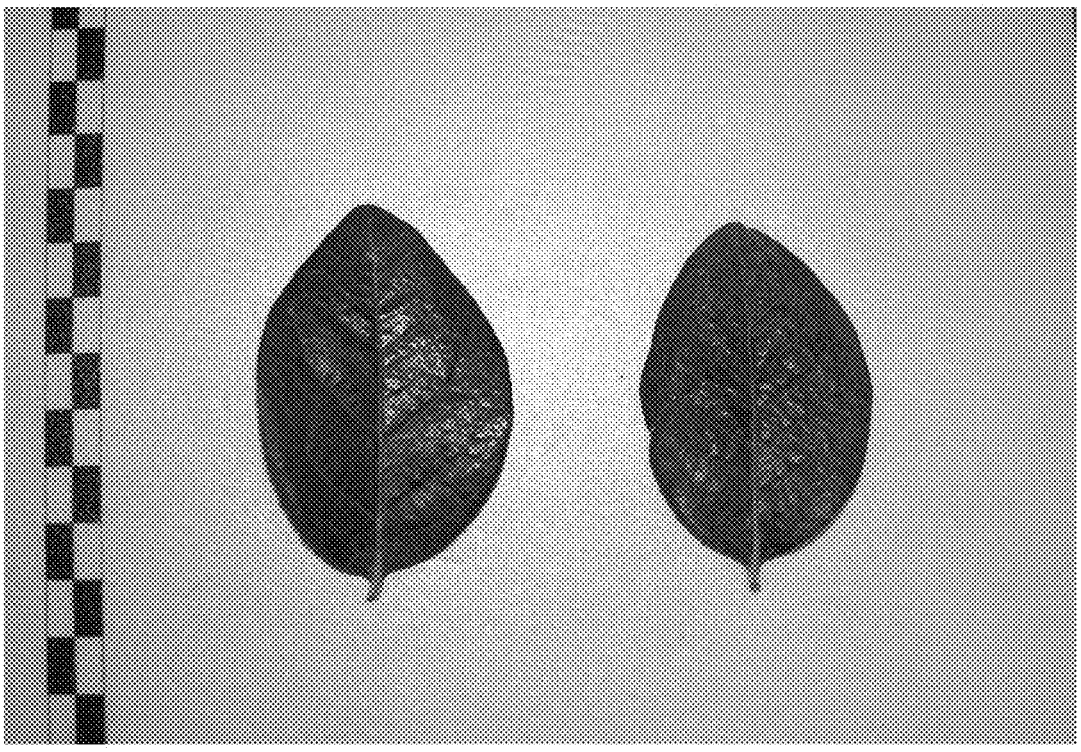
FIG. 4.—Shows the upper sides and shape of complete leaves on 2-year-old plant of the new variety 'BLUECSOL12'.
Figure 5:
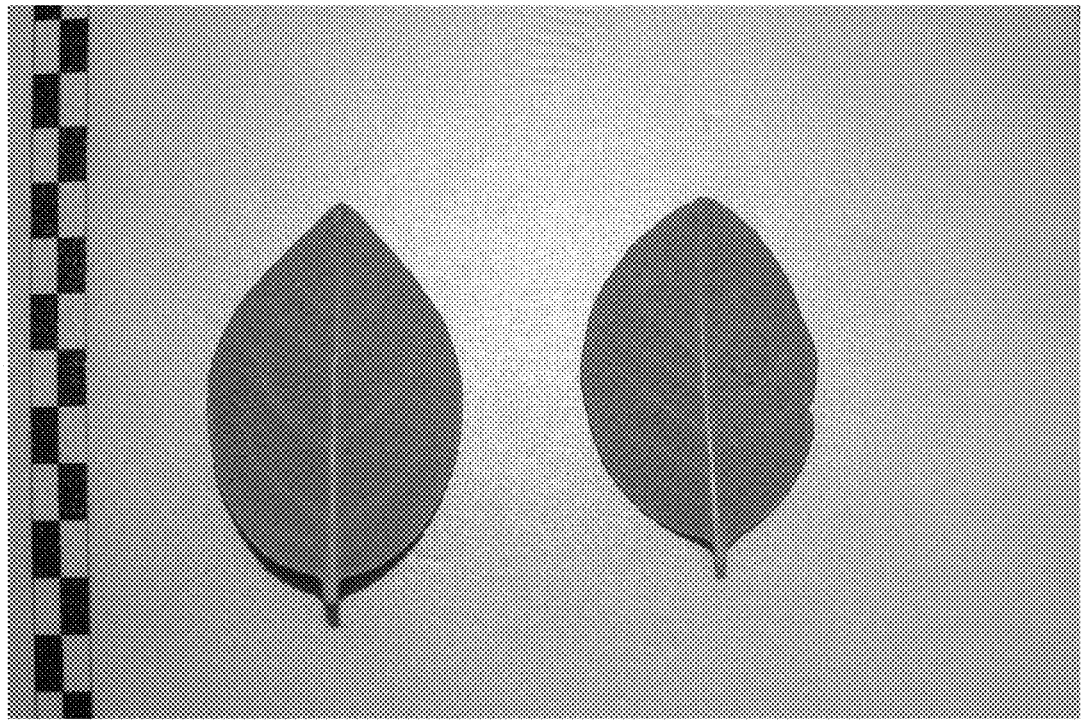
FIG. 5.—Shows the underside of a complete leave on 2-year-old plant of the new variety 'BLUECSOL12'.
Figure 6:
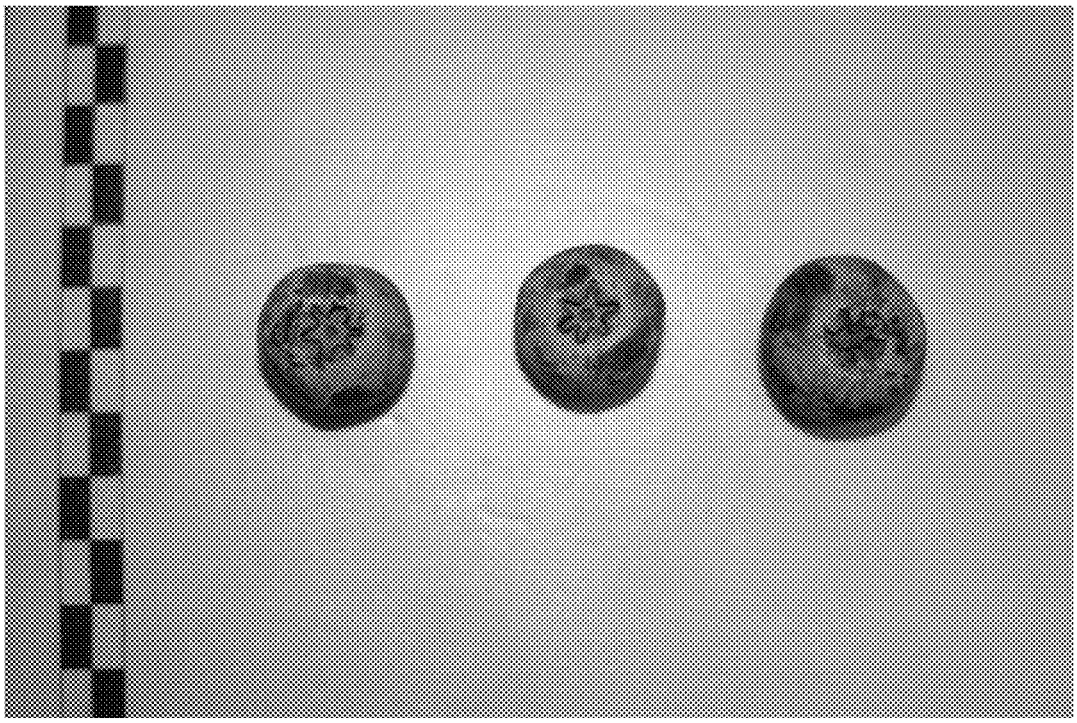
FIG. 6.—Shows the size and shape of the fruits on 2-year-old plant of the new variety 'BLUECSOL12'.

The following botanical description detailed forth distinctive traits of 'BLUECSOL12'. The data were collected from clones stablished in an experimental test plot in Peru on 2-year-old plants. Color descriptions are based on the Munsell® Plant Tissue Color Book scale and Pantone® color codes.

Classification:
- *Family*.—Ericaceae.
- *Genus*.—*Vaccinium*.
- *Specie*.—*Vaccinium corymbosum* L.
- *Common name*.—Southern Highbush Blueberry.
- *Variety name*.—'BLUECSOL12'.

Parentage:
- *Female parent*.—'Biloxi' (Public plant).
- *Male parent*.—Unidentified variety.

Plant:
- *Vigor*.—Exceeds 'Emerald' (U.S. Plant Pat. No. 12,165) and 'Biloxi' (Public plant).
- *Growth habit*.—Upright.
- *Time of beginning of vegetative growth*.—Medium.
- *Time of beginning on one-year-old shoot*.—Medium.
- *Height*.—Mean of 104 cm.
- *Width*.—Mean of 82 cm.
- *Internode length*.—Mean of 35.9 mm.
- *Color of 1-year-old rough bark observed December* 22.—Green Munsell® 5GY 6/6.
- *1-year-old wood length*.—Mean of 45 cm.
- *The mature cane's color observed July* 23.—Brown Munsell® 5YR 4/4.
- *The mature cane's length*.—About 30 to 40 cm.
- *Surface texture of the mature cane*.—Rough.
- *Chilling requirements*.—0 hours below 7° C.
- *Evergreenness*.—Evergreen.

Propagation:
- *Ease of propagation*.—Propagates readily from softwood cuttings and tissue culture.
- *Type*.—By In vitro culture.
- *Root description*.—'BLUECSOL12' develops deep root systems and medium volume of roots in the topsoil layer.
- *Rooting habit*.—Moderate density and branching.

Leaves:
- *Length*.—Mean of 74 mm.
- *Width*.—Mean of 53 mm.
- *Length/width ratio*.—1.41.
- *Shape*.—Ovate.
- *Shape of the apex*.—Ovate.
- *Shape of the base*.—Ovate.
- *Surface texture in the upper*.—Leathery and shiny.
- *Surface texture in the lower*.—Waxy and smooth.
- *Margin*.—Serrate.
- *Color on upper side of old leaves*.—Green Munsell® 5GY 3/4.
- *Color on upper side of young leaves*.—Green Munsell® 5GY 4/6.

Petiole:
- *Length*.—Mean of 3.9 mm.
- *Texture*.—Smooth.
- *Color*.—Green Munsell ® 5GY 7/6.

Flowers:
- *Flower cluster*.—Medium.
- *Flower fragrance*.—Faint smell of roses flower.
- *Inflorescence length*.—Mean of 5.5 cm.
- *Inflorescence diameter*.—Mean of 2.4 cm.

Corolla:
- *Size of corolla tube*.—Mean of 21.7 mm (from pedicel attachment point to corolla tip excluding the pedicel).
- *Corolla shape*.—Campanulate.
- *Corolla tube color*.—White Pantone® 11-0601 TPX.

Stamen:
- *Length*.—Mean of 0.7 cm.
- *Number per flower*.—About 10 to 12.
- *Color of filament*.—Green Munsell ® 2.5GY 8/4.
- *Color of anther*.—Yellow Munsell ® 7.5YR 7/10.

Pistil:
- *Number per flower*.—1.
- *Style color*.—Green Munsell ® 5GY 6/6.
- *Style length*.—Top of ovary to stigma tip. 9 mm.

Pollen:
- *Color*.—Yellow Munsell ®5Y 7/2.
- *Abundance*.—High.

Fruits:
- *Fruiting type*.—one-year-old and current seasons shoots.
- *Time of beginning of fruit ripening on one-year-old shoot*.—Early.
- *Time of beginning of fruit ripening on current season's shoot*.—Early.
- *Diameter of calyx aperture on mature berry*.—Mean of 5.6 mm.
- *Diameter of depth of calyx on mature berry*.—Mean of 2.5 mm.
- *Detachment force for ripe berries* (*easy, medium, hard*).—Easy.
- *Berries per cluster*.—About 8 to 14.
- *Width*.—About 18 to 26 mm.
- *Weight*.—Mean of 4.6 g per berry.
- *Shape*.—Oblate.
- *Intensity of fruit bloom*.—Medium.
- *Pedicel scar*.—Mean of 2.5 mm.
- *Color of unripe fruit*.—Light green Munsell® 5GY 5/6.
- *Color of mature fruit skin with bloom*.—Dapple gray Pantone® 16-3907 TCX.
- *Color of mature fruit skin without bloom*.—Dark navy Pantone® 19-4013 TCX.
- *Fruit flesh color*.—Green yellow Munsell® 2.5GY 8/6.
- *Fruit firmness*.—Firm.
- *Fruit acidity*.—High.

*Fruit sweetness*.—High.

*Market use of fruit*.—Fresh market.

Seeds:

*Color*.—Brown Munsell® 5YR 4/6.

*Seeds per berry*.—Mean of 11 seeds.

Reproductive organs:

*Pollen abundance*.—High.

*Disease, insects, and mites*.—No sensitivity to any disease and pest has been observed for 'BLUECSOL12'.

Plant hardiness zone: The plants of the 'BLUECSOL12' variety were tested under the arid conditions of the northern coast of Peru, where the maximum temperatures in the year are 32° C. and the minimum are 13° C. The 'BLUECSOL12' variety can produce fruit all year round and does not require temperatures below 7° C. for flower induction. The area where its behavior was observed and evaluated does not have extreme temperatures to be able to determine cold or heat resistance.

Productivity: 'BLUECSOL12' has a medium to high productive potential. The harvest begins after 6 months of the planting or pruning of the plants on the field and lasts for 24 weeks. Plant productivity in the first season is about 1.5 to 2.5 kg per plant and in the second season is around 2.0 to 3.0 kg per plant. 80% of the harvest is concentrated in 19 weeks.

Storage qualities: 'BLUECSOL12' has a shelf life of more than 49 days under modified atmosphere storage at 1° C. and 35 days under controlled atmosphere storage at 1° C.

COMPARISON TO THE PARENT

'BLUECSOL12' is distinguished from 'Biloxi' variety in the following characteristics:

The vigor of 'BLUECSOL12' is greater than 'Biloxi' (Public plant).

The length of the Inflorescence (excluding peduncle) in 'BLUECSOL12' is smaller than 'Biloxi' (Public plant).

Shape of the corolla in 'Biloxi' (Public plant) is globose, whereas in 'BLUECSOL12' is campanulate.

1Length of the corolla in 'Biloxi' (Public plant) is less than 'BLUECSOL12'.

Fruit size of 'Biloxi' (Public plant) is medium, whereas in 'BLUECSOL12' fruit size is extra-large.

Diameter of calyx basin in berries of 'Biloxi' (Public plant) is smaller than 'BLUECSOL12'.

Depth of calyx basin in berries of 'Biloxi' (Public plant) is greater than 'BLUECSOL12'.

COMPARISON TO CLOSEST VARIETY

'BLUECSOL12' is distinguished from 'BLUECSOL5' (U.S. Plant patent application Ser. No. 17/803,891) variety in the following characteristics:

The rooting habit of 'BLUECSOL12' is moderate density and branching, whereas in 'BLUECSOL5' is high density and branching.

The leaf width of 'BLUECSOL12' is greater than 'BLUECSOL5'.

The texture of the upper and lower surface of the leaf in 'BLUECSOL5' is waxy, whereas in 'BLUECSOL12' is leathery and shiny.

Fruit firmness in 'BLUECSOL12' is lower than the fruit firmness in 'BLUECSOL5'.

'BLUECSOL12' has less seeds per fruit than 'BLUECSOL5'.

The abundance of pollen in 'BLUECSOL12' is greater than 'BLUECSOL5'.

COMPARISON TO COMMERCIAL VARIETY

The vigor of 'BLUECSOL12' is greater than 'Emerald' (U.S. Plant Pat. No. 12,165)

Shape of corolla is cylindric in 'Emerald' (U.S. Plant Pat. No. 12,165), whereas in 'BLUECSOL12' is campanulate.

The margin of the leaf of 'BLUECSOL12' is serrate, whereas in 'Emerald' (U.S. Plant Pat. No. 12,165) is entire.

The depth of the calyx basin on mature berry in 'BLUECSOL12' is less than in 'Emerald' (U.S. Plant Pat. No. 12,165).

Fruit firmness in 'BLUECSOL12' is greater than 'Emerald' (U.S. Plant Pat. No. 12,165).

Intensity of fruit bloom in 'Emerald' (U.S. Plant Pat. No. 12,165) is weaker than 'BLUECSOL12'.

The abundance of pollen in 'Emerald' (U.S. Plant Pat. No. 12,165) is greater than 'BLUECSOL12'.

What is claimed is:

1. A new and distinct blueberry plant named 'BLUECSOL12' substantially as illustrated and described.

* * * * *